(12) United States Patent
Behringer

(10) Patent No.: US 7,056,472 B1
(45) Date of Patent: Jun. 6, 2006

(54) DEVICE FOR FEEDING A TREATMENT LIQUID TO MEDICAL APPLIANCES

(75) Inventor: Wolfgang Behringer, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 297 days.

(21) Appl. No.: 10/362,125

(22) PCT Filed: Aug. 22, 2000

(86) PCT No.: PCT/DE00/02861

§ 371 (c)(1),
(2), (4) Date: Feb. 21, 2003

(87) PCT Pub. No.: WO02/15811

PCT Pub. Date: Feb. 28, 2002

(51) Int. Cl.
*C02F 1/50* (2006.01)
(52) U.S. Cl. .......................................... 422/28; 433/82
(58) Field of Classification Search ................. 433/80, 433/82, 84, 27, 28, 98, 99, 100; 210/267; 422/3, 28, 31
See application file for complete search history.

(56) References Cited

U.S. PATENT DOCUMENTS

| | | | |
|---|---|---|---|
| 4,545,956 A | 10/1985 | Ciszewski et al. | 422/28 |
| 5,087,198 A | 2/1992 | Castellini | 433/80 |
| 5,295,829 A * | 3/1994 | Frey et al. | 433/82 |
| 5,558,841 A * | 9/1996 | Nakagawa et al. | 422/105 |
| 5,785,523 A * | 7/1998 | Overmyer | 433/82 |
| 6,177,018 B1 * | 1/2001 | Ruppenthal | 210/739 |

FOREIGN PATENT DOCUMENTS

| | | |
|---|---|---|
| DE | 36 35 568 | 8/1987 |
| DE | 195 09 180 | 9/1996 |

* cited by examiner

*Primary Examiner*—Todd E. Manahan
(74) *Attorney, Agent, or Firm*—Dykema Gossett PLLC

(57) ABSTRACT

A device for feeding a treatment liquid into medical appliances. The device includes an outlet opening for the treatment liquid, especially for feeding water into dental equipment, a feed line for the treatment liquid, means to introduce degerminating agents into the treatment liquid, and an on/off valve disposed upstream from an outlet opening onto which the feed line is connected. A back-flush valve is connected to the on/off valve, and a reservoir is provided for the treatment liquid, whereby the treatment liquid is transported from the reservoir with the aid of a pump. Further, a back-flush line is connectible alternatively via a drain valve to a drain or to the reservoir so that the treatment liquid is pumped into the drain, or in circulation from the reservoir through the feed line to the switch valve and through the back-flush line again into the reservoir.

12 Claims, 1 Drawing Sheet

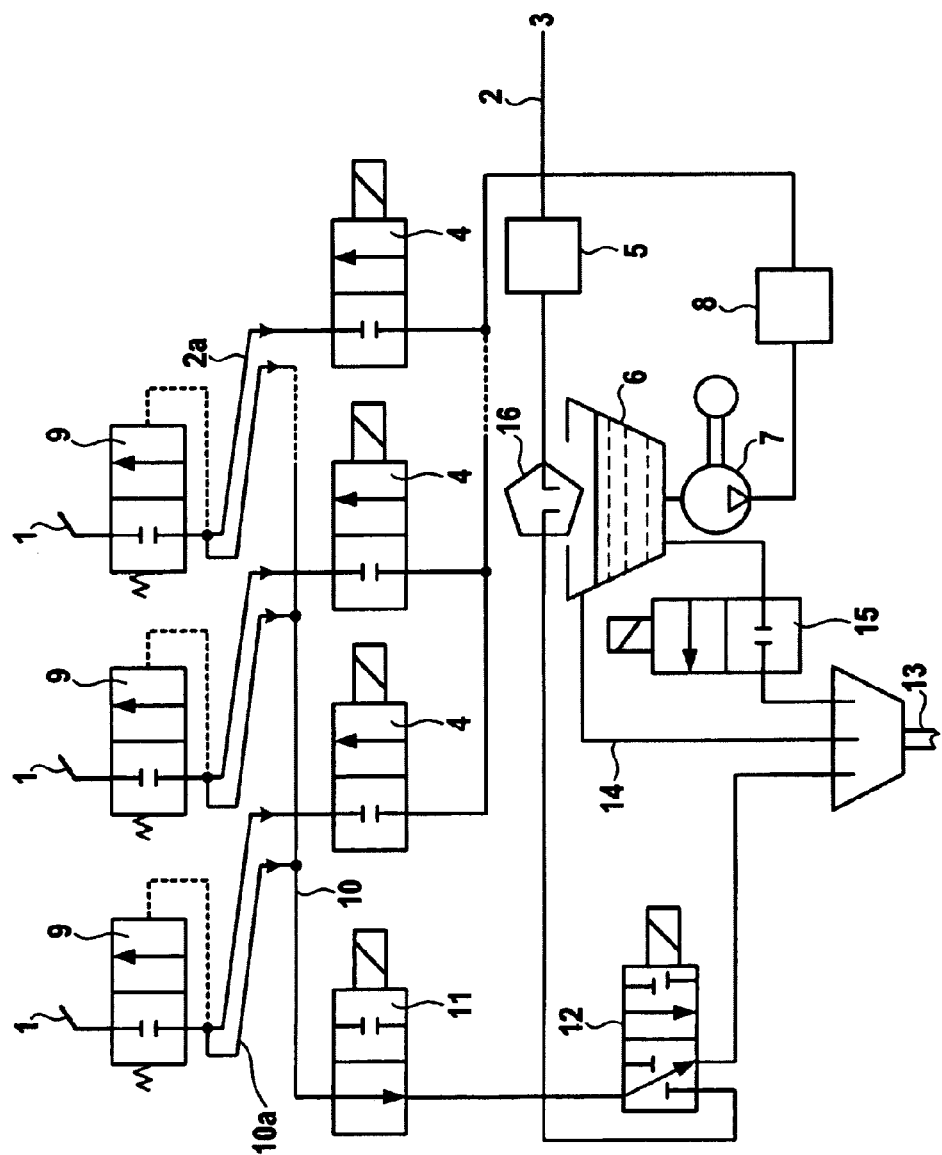

DEVICE FOR FEEDING A TREATMENT LIQUID TO MEDICAL APPLIANCES

The invention relates to a device for feeding a treatment liquid to medical appliances comprising an outlet opening for the treatment liquid, especially for feeding water into dental equipment, and a feed line for the treatment liquid as well as means for introducing degerminating agents into the treatment liquid.

Medical appliances are well known in practice to be used in different applications through which a treatment liquid is applied. Microbial contamination of the treatment liquid is to be absolutely prevented, especially in the medical field. Problems occurring in this connection are described below in an example of a dental treatment unit—a so-called dental equipment having a cooling liquid supply and an irrigation liquid supply.

As a rule, dental equipment uses drinking water as cooling and irrigation liquid that is drawn from the local water supply net. Even at the connection point of the drinking water supply and the dental equipment, there is often found a bacteria count that is far above the limit of 100 colony-forming units per milliliter (KBE/ml) determined by the drinking water ordinance and there are often times detected problematic bacteria such as "*Pseudomonas aeruginosa*" or "*Legionella*". In addition, dental treatment units have particular features in contrast to the drinking water system, which promote bacteria growth and causes a high bacteria count thereby.

Dental treatment units include normally a plurality of handpieces with different treatment adapters whereby each handpiece is connected to an individual tap. Often times, water remains in the treatment unit for a relative long time based on the different use of the individual handpieces, during breaks in treatment, and during the weekend, which causes stagnation of water. Standing water is thereby warmed up to room temperature. In addition, water is brought to body temperature before the application. Bacteria growth is promoted further by small hoses, constrictions in cross sections and formation of dead space, e.g. in valves. Additionally, it must be considered that most of the water-conducting components and hoses of dental treatment units are made of synthetic material whereby they provide an ideal nutritive medium for bacteria growth because of the large surface per water volume.

Sterilization of the drinking water before application is therefore advisable or even absolutely necessary. Sterilization units or measures are employed in practice which introduce either a suitable degerminating (antimicrobial) agent into the drinking water at a particular dosage or which cause sterilization through an electrolytical process, for example.

It has been shown, however, that bacteria growth cannot be completely prevented with the aid of sterilization units of the prior art since bacteria growth increases in the line at a distance away from the sterilization unit. Overall, re-contamination cannot be reliably prevented with the use of sterilization units of the prior art.

Some manufacturers of dental equipment offer therefore so-called conditioning programs. In the scope of these conditioning programs, highly concentrated degerminating agents are pumped through the entire dental equipment, through each outlet and each handpiece, and they are then left in the lines of the dental equipment for several hours. The dental equipment is subsequently flushed with drinking water until the concentration of the degerminating agent is reduced to a level that is harmless for the patient.

Completion of a conditioning program, as described above, normally takes 12 to 24 hours during which time the dental equipment cannot be used. Re-contamination can be effectively prevented only by regular use of the above-mentioned program since there is currently no possibility to determine the degree of microbial contamination of the dental equipment and to discern if conditioning is actually necessary.

In the German laid-open patents 32 46 266 and 36 35 568 are disclosed devices for the disinfection of water paths in dental appliances providing periodic flushing of the water paths with a disinfectant. In both cases, there are feed lines provided for the treatment liquid and means to introduce degerminating agents into the treatment liquid. Valves are assigned to the outlet opening in the feed line of the disclosed arrangement.

The object of the German laid-open patent 195 09 180 A1 is an arrangement to clean at least one so-called drive pathway in a medical handpiece, particularly a dental handpiece. In this arrangement there are valves provided for each of the feed lines. In addition, there is a special non-return valve arranged in a connecting line.

The object of U.S. Pat. No. 5,087,198 is a dental appliance into which a treatment liquid can also be fed. This appliance comprises three-way valves disposed upstream for switching the treatment liquids.

SUMMARY OF THE INVENTION

The inventive device achieves the above object through the characteristics of patent claim 1. Accordingly, the aforementioned device is designed in a manner whereby an on/off valve is disposed upstream of the outlet opening onto which the feed line is connected, and whereby a back-flush line with a back-flush valve is connected to the on/off valve.

The present invention has now the object to provide a device for feeding a treatment liquid into medical appliances of the aforementioned type with which microbial contamination or re-contamination can be prevented in a simple but effective manner.

The inventive device achieves the above object through the characteristics of patent claim 1. Accordingly, the aforementioned device is designed in a manner whereby a switch valve is disposed upstream of the outlet opening onto which the feed line is connected, and whereby a back-flush line with a back-flush valve is connected to said switch valve.

According to the invention, it has been observed that re-contamination can be effectively prevented with the use of sterilization units of the prior art if the treatment liquid, which is fed through the medical appliance and which is then enriched with a degerminating agent, is not necessarily dispensed via the outlet opening of the medical appliance but can be used alternatively for flushing of the medical appliance. For this purpose, an on/off valve is placed upstream of the outlet opening, according to the invention, onto which there is connected the feed line as well as a back-flush line with its back-flush valve so that the feed line can be alternatively connected to the outlet opening or the back-flush line. The treatment liquid, which is enriched with degerminating agents, flows through the feed line up to the switch valve and via the switch valve into the back-flush line to flush the medical appliance. Thereby the back-flush valve is opened.

Since the treatment liquid enriched with degerminating agents can be either simply applied through the outlet opening, based on the inventively proposed constructive measures, or be used for flushing of the appliance, there is also the possibility to flush the medical appliance according to needs, e.g. directly before application of the treatment liquid, during treatment breaks, or before daily operational use.

The valve concept of the inventively proposed device for feeding a treatment liquid may be basically realized with the use of various types of valves.

The on/off valve and the back-flush valve may thereby be designed as one, which means as a three-way valve disposed upstream from the outlet opening, with which either the outlet opening or the back-flush line can be selectively connected to the feed line.

In most medical appliances and particularly in dental equipment, the possibly smallest instrument size should be the goal, especially the region of the outlet opening in which the on/off valve is arranged. It is of advantage thereby to arrange the back-flush valve in the back-flush line itself, which means offset relative to the on/off valve. A pressure-controlled valve can be used in this case as a on/off valve that closes and opens, depending on the switched position of the back-flush valve in the back-flush line and the thereby associated pressure conditions in the back-flush line. In contrast to other types of valves, e.g. electrical on/off valves, there are no additional controlling means necessary, such as wires etc, which would have a negative impact on the size of the on/off valve.

It is of great advantage to realize the on/off valve as a non-return valve. Reverse suction via the outlet opening can be prevented thereby, including the associated infiltration of fluid and bacteria into the medical appliance.

As mentioned above, the inventive device for feeding a treatment liquid into medical appliances comprises means to introduce degerminating agents into the treatment liquid whereby this could be a sterilization unit already well known in practice. In an especially preferred embodiment of the inventive device there are provided additional means for determining the type and/or amount of bacteria existing in the treatment liquid or in the medical appliance so that there can be determined, on an individual basis, the type and dosage of the degerminating agent to be added as well as the back-flush period. In addition, means can be provided to determine the concentration or possibly the type of degerminating agent in the treatment liquid so that the dosage of the degerminating agent added to the treatment liquid can be monitored or possibly also controlled. It can be easily determined thereby whether the degerminating agent has been used up by consumption during a period of standstill. Should there be means provided to regulate the concentration of the degerminating agent in the treatment liquid, then the medical appliance can also be directly flushed with treatment liquid that has a degerminating agent added at a higher concentration than the one that is proposed for application.

It is furthermore advantageous to provide a reservoir for the treatment liquid and to transport the treatment liquid with the aid of a pump from the reservoir. In this case, the treatment liquid could be enriched in the reservoir with at least one degerminating agent with the aid of a dosage device assigned to the reservoir so that an additional sterilization unit would not be needed in the feed line. An additional sterilization unit disposed upstream from the reservoir would have the advantage that the reservoir as well as the pump could be sterilized together. A sterilization unit of this type could also be used as an alternative to the dosage device assigned to the reservoir.

The back-flush line is alternatively connectable via a drain valve to a drain or to the reservoir in the inventive device so that the treatment liquid can be pumped alternatively into the drain during flushing of the medical appliance or it can be pumped in circulation from the reservoir through the feed line to the on/off valve—and via the back-flush line again into the reservoir. The possibility to pump the treatment liquid enriched with degerminating agents in circulation through the device and the medical appliance is especially advantageous when a flushing process is necessary with higher concentrated degerminating agents.

One should be able to empty the reservoir directly in an advantageous manner to flush sediments from the reservoir, for example. In a preferred embodiment of the inventive device, there could be provided a drain valve for this purpose.

BRIEF DESCRIPTION OF THE DRAWING

There are now various possibilities to design and develop the device in an advantageous manner according to the theory of the present invention. This is shown, on one hand, in the subordinate claims of patent claim 1, and, on the other hand, in the following description of an embodiment of the invention and with the aid of the drawing.

The single drawing shows in a schematic illustration a device according to the invention for feeding water into a dental treatment unit.

The dental treatment unit (not further identified in the single drawing) is thereby connected via a feed line 2 to the local drinking water supply 3—and the individual hand pieces or the dental instruments 1 are connected parallel to the feed line 2 via assigned supply valves 4 and feed line sections 2a.

In the hereby illustrated embodiment, the drinking water drawn from the water supply 3 passes through a sterilization unit 5 arranged in the feed line 2, wherein it is enriched with a degerminating agent, and then flows into a reservoir 6. From there, the liquid is urged with the aid of a pump 7 through an additional sterilization unit 8 to the individual dental instruments 1.

DETAILED DESCRIPTION OF THE INVENTION

In the drawing, the dental treatment unit has three hand-pieces for different dental instruments 1. Each of these dental instruments 1 is provided with an outlet opening through which water may be applied as a cooling and/or irrigation liquid during treatment of a patient. Accordingly, the dental instruments 1 must be supplied with water at least during the treatment of the patient.

According to the invention, an on/off valve 9 is disposed upstream from the outlet opening of each dental instrument 1 whereby the feed line 2 or the respective feed line section 2a is connected to valve 9. A back-flush line 10a, 10 together with a back-flush valve 11 is connected to the switch valve 9 in addition to the feed line 2.

According to the illustrated embodiment, the on/off valves 9 of the individual dental instruments 1 are very near to the respective outlet opening so that each dental instrument 1 has its own back-flush line section 10a running parallel to the respective feed line section 2a in the assigned handpiece hose. The back-flush line sections 10a of the individual dental instruments 1 are then connected to a mutual back-flush line 10 in which the back-flush valve 11 is arranged as well. Alternatively thereto, a back-flush valve of the respective dental instrument could also be arranged in each back-flush line section 10a.

The on/off valves 9 of the individual instruments 1 are here designed as non-return valves so that suction of liquid through the outlet opening of a dental instrument 1 is prevented and thereby prevented is thereby also the associated migration of bacteria into the treatment unit. In addition, the valves 9 in the illustrated embodiment are all pressure controlled. The switched position of the valves 9 depends here also on the switched position of the supply valve 4 of the respective dedicated dental instrument 1, on the one hand, and on the switched position of the back-flush valve 11, on the other hand. At first, the respective supply valve 4 is opened at employment of one of the three existing dental instruments. While the back-flush valve 11 is simultaneously closed, a back pressure develops in the back-flush line 10 or in the back-flush line section 10a of the dental instrument 1, which in turn effects the opening of the assigned valve 9 so that the water can be applied through the outlet opening of the dental instrument 1. Should the back-flush valve 11 also be opened while the supply valve 4 is open, then the switch valve 9 closes automatically. The water enriched with degerminating agents is then pumped through the feed line 4 into the dental instrument 1 and up to the valve 9 and then the liquid flows from there through the back-flush line 10a, 10, the back-flush valve 11 and the drain valve 12 alternatively either into the drain 13 or back into the reservoir 6—depending on the switched position of the drain valve 13—from where the liquid can be pumped again in circulation to the dental instrument 1 and back into the reservoir 6. This flushing process can then be repeated as often as desired whereby the supply of water enriched with degerminating agents is pumped continuously at set intervals through the line system of the treatment unit.

The reservoir 6 is additionally provided with an overflow 14 in the illustrated embodiment example, which also leads to the drain 13. The reservoir 6 can be emptied directly into the drain 13 through a drain valve 15.

Finally, there is still a measuring probe 16 arranged in the feed line 2 between the sterilization unit 5 and the reservoir 6, which serves to determine the concentration and possibly the type of degerminating agent in the treatment liquid so that the dosage of the degerminating agent infused in the treatment liquid can be monitored and possibly controlled as well. Designed appropriately, the measuring probe 16 could be used to determine the type and/or amount of existing bacteria and to individually determine the type and dosage of the degerminating agent to be infused and to individually determine the time for the back-flush process.

The back-flush valve 11 is opened at first to flush the entire line system after turning on the treatment unit. The supply valve 4, which is the greatest distance away from the sterilization unit 8, is subsequently opened to flush for a sufficient period the feed line 2, the feed line section 2a and the back-flush line section 10 of the dental instrument 1 that is the greatest distance away from the sterilization unit 8, as well as the return line 10 with its back-flush valve 11. Now, the supply valve 4 of the first dental instrument 1 will be closed again and the supply valve 4 of the next dental instrument 1 is opened. During this flushing process, only the volume in the respective feed line section 2a and the one in the back-flush line section 10a has to be exchanged. The process is continued until the feed line section 2a and the back-flush line section 10a of all dental instruments 1 have been flushed. It is ensure thereby that the entire line system is supplied with degerminating agents. The above-described flushing process is repeated in all handpieces or dental instruments that were out of operation long enough relative to a period of standstill best suited for the degerminating agent.

Bacteria growth can be prevented in the entire line system of the treatment unit in a simple but reliable manner with the above-described device whereby the entire line system is flushed with the treatment liquid into which degerminating agents are infused at a relatively low dosage.

What is claimed is:

1. A device for feeding a treatment liquid into medical appliances comprising an outlet opening for said treatment liquid, said device comprising:
   a feed line for said treatment liquid,
   means to introduce degerminating agents into said treatment liquid,
   at least one switch valve disposed upstream from the outlet opening onto which said feed line is connected,
   wherein a back-flush line with at least one back-flush valve is connected to said switch valve, and wherein a reservoir is provided for said treatment liquid, whereby said treatment liquid is transported from said reservoir with the aid of a pump, and wherein the back-flush line is connectible alternatively via a drain valve to one of a drain and to said reservoir so that the treatment liquid is pumped into said drain, or is circulated from said reservoir through said feed line to said switch valve and through said back-flush line again into said reservoir.

2. A device according to claim 1, wherein said switch valve and said back-flush valve together act as a three-way valve disposed upstream from said outlet opening.

3. A device according to claim 1, wherein said back-flush valve is arranged in the back-flush line and wherein said switch valve is pressure-controlled so that it opens up while said back-flush valve is closed based on the back pressure developing in said back-flush line and whereby said switch valve closes while said back-flush valve is in an open position.

4. A device according to claim 1, wherein said switch valve comprises a non-return valve.

5. A device according to claim 1, wherein means to determine the type and/or amount of existing germs is provided to determine the type and dosage of the degerminating agent to be infused as well as the time for the back-flush process.

6. A device according to claim 1, wherein means are provided to determine the concentration and the type of the degerminating agent in the treatment liquid so that the dosage of the degerminating agent infused in said treatment liquid may be monitored and controlled.

7. A device according to claim 1, wherein said reservoir has a dosage device dedicated for at least one degerminating agent so that said degerminating agent can be added to the treatment liquid in said reservoir.

8. A device according to claim 1, wherein a sterilization unit is disposed upstream from said reservoir.

9. A device according to claim 1, wherein a drain valve is provided through which said reservoir can be emptied directly.

10. A device according to claim 1, wherein a plurality of handpieces of the medical appliance are connected parallel to said feed line for the treatment liquid via respective supply valves, and wherein back-flush line sections extending from switch valves of the individual handpieces lead into said back-flush line.

11. A device according to claim 10, wherein said handpieces respectively have back-flush valves.

12. A device according to claim 10, wherein a common back-flush valve is provided in said back-flush line for all connected handpieces.

* * * * *